(12) United States Patent
Ali et al.

(10) Patent No.: US 10,751,376 B1
(45) Date of Patent: Aug. 25, 2020

(54) METHOD FOR TREATING CANCER

(71) Applicant: Jassim M. Hassan M. Ali, Safat (KW)

(72) Inventors: Jassim M. Hassan M. Ali, Safat (KW); Peiying Yang, Houston, TX (US)

( * ) Notice: Subject to any disclaimer, the term of this patent is extended or adjusted under 35 U.S.C. 154(b) by 20 days.

(21) Appl. No.: 16/293,283

(22) Filed: Mar. 5, 2019

(51) Int. Cl.
*A61K 35/60* (2006.01)
*A61K 47/02* (2006.01)
*A61K 9/00* (2006.01)
*A61P 35/00* (2006.01)

(52) U.S. Cl.
CPC ............ *A61K 35/60* (2013.01); *A61K 9/0019* (2013.01); *A61K 47/02* (2013.01); *A61P 35/00* (2018.01)

(58) Field of Classification Search
None
See application file for complete search history.

(56) References Cited

U.S. PATENT DOCUMENTS

| | | | |
|---|---|---|---|
| 5,658,594 A | 8/1997 | Al-Hassan |
| 5,912,018 A | 6/1999 | Al-Hassan |
| 8,551,532 B2 | 10/2013 | Al-Hassan |

OTHER PUBLICATIONS

Al-Hassan et al., "Skin Preparations from Catfish (*Arius bilineatus*, Val.) Contain a Lipid Which Inhibits Cancer Cell Survival In Vitro," The FASEB Journal, vol. 30, No. 1 supplement, Apr. 1, 2016.
Yang et al., "Abstract 2246: Anti-proliferative activities of lipid fraction of extract from the skin of the catfish *Arius bilineatus*, Valenciennes," AACR Annual Meeting 2017; Apr. 1-5, 2017, Washington, DC.
Yang et al., "Anti-proliferative and anti-invasiveness of the lipid fraction of the skin extract from the catfish *Arius bilineatus*, valenciennes in human pancreatic cancer is associated with regulation of lipid metabolism," Cancer Research 77, (13 Supplement):2246-2246, Jul. 2017.

*Primary Examiner* — Christina Bradley
(74) *Attorney, Agent, or Firm* — Richard C. Litman; Nath, Goldberg & Meyer

(57) ABSTRACT

A method of treating cancer can include administering a therapeutically effective amount of a composition comprising a soluble protein fraction obtained from epidermal gel secretions of catfish to a patient in need thereof. The soluble protein fraction can include soluble proteins and lipids from the epidermal gel secretions of catfish. The soluble protein fraction can include about 87% of the soluble proteins and about 13% of the lipids. The cancer can include at least one of liver cancer and pancreatic cancer. The composition can be administered by intraperitoneal (IP) or sub-cutaneous (SC) injection.

6 Claims, 9 Drawing Sheets

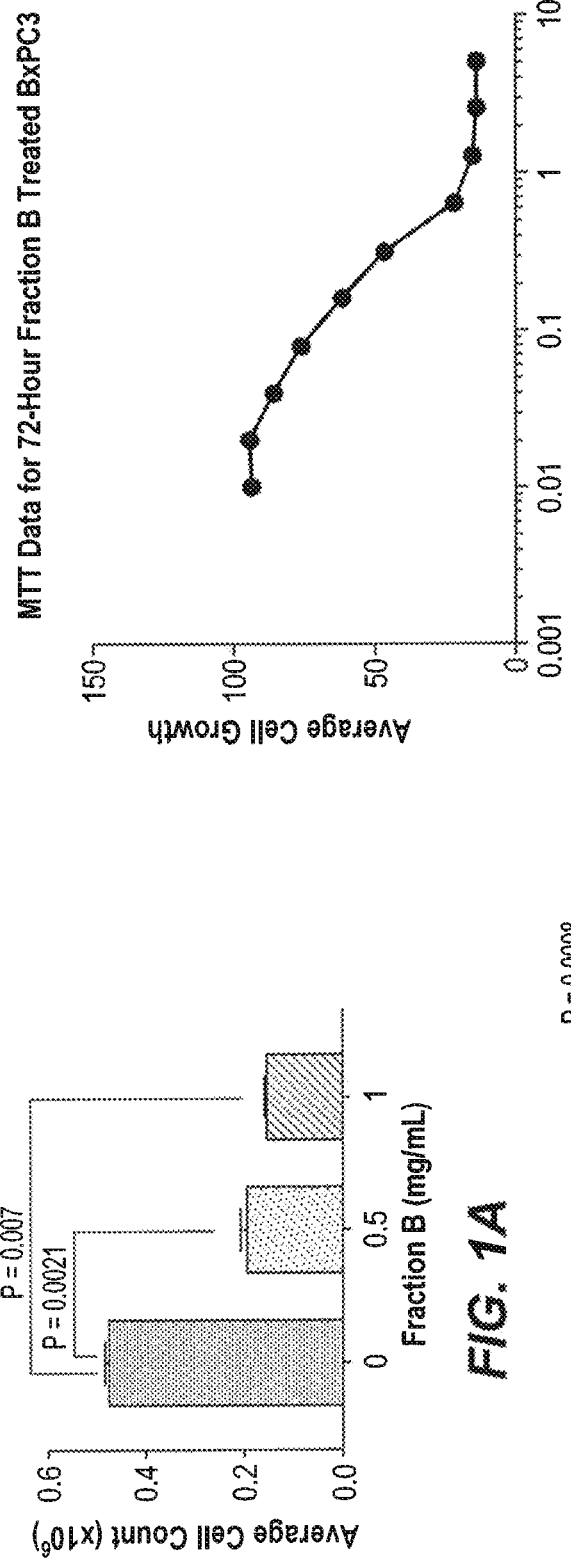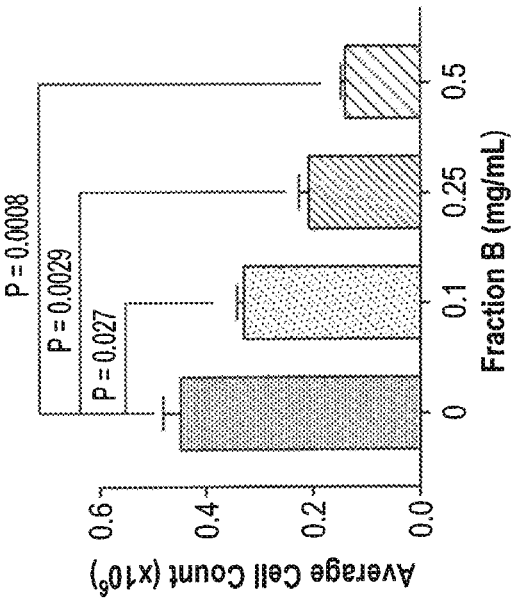

METHOD FOR TREATING CANCER

BACKGROUND

1. Field

The disclosure of the present patent application relates to use of a preparation from the epidermal gel secretions of catfish for therapeutic purposes, and particularly, to a method for treating pancreatic cancer using the preparation from the epidermal gel secretions of catfish.

2. Description of the Related Art

Pancreatic cancer is a disease that is very difficult to cure and is considered one of the deadliest forms of cancer. Conventional drugs for treating pancreatic cancer are costly and associated with numerous side effects. For example, many conventional drugs are toxic to the blood and other internal organs. In addition, these drugs are only modestly effective.

The Arabian Gulf catfish (*Arius bilineatus* (Valenciennes)) naturally exudes a proteinaceous gel-like material ("epidermal gel secretion" or "EGS") from its epidermis upon stress or injury. The epidermal gel secretion includes a complex mixture of biochemically and pharmacologically active components, such as soluble proteins, lipids, and insoluble proteins.

The epidermal gel secretion can provide numerous therapeutic benefits. Often times, however, the Arabian Gulf catfish produces venoms from its venomous spines and venom glands near its pectoral spines which mix with secretions on the catfish skin. Additionally, since the gelatinous secretion is exuded while the catfish is still alive, contaminants other than the venom (such as feces, vomit and blood) are also often mixed with the epidermal secretion.

Thus, a method of treating pancreatic cancer solving the aforementioned problems is desired.

SUMMARY

A method of treating cancer can include administering a therapeutically effective amount of a composition comprising a soluble protein fraction obtained by fractionating epidermal gel secretions of catfish to a patient in need thereof. The soluble protein fraction can include soluble proteins and lipids obtained by fractionating the epidermal gel secretions of catfish. The soluble protein fraction can include about 87% soluble proteins and about 13% lipids. The cancer can include at least one of liver cancer and pancreatic cancer. The composition can be administered by intraperitoneal (IP) or sub-cutaneous (SC) injection. A method of preparing the soluble protein fraction can include collecting the epidermal gel secretion of catfish and fractionating the epidermal gel secretion to obtain the soluble protein fraction.

Fractionating the epidermal gel secretion of catfish can include mixing the catfish epidermal gel secretions with phosphate buffered saline to provide an extract, homogenizing the extract to provide a homogenized extract, and centrifuging the homogenized extract to provide a soluble protein fraction and an insoluble protein fraction. The soluble fraction can be freeze dried to provide a powdered soluble fraction. If desired, the insoluble protein fraction can be fractionated (in the manner described above for fractionating the EGS) to separate any undissolved soluble proteins therefrom. The additional soluble protein fraction extracted from the insoluble protein fraction can be added to the original soluble protein fraction to enrich the original soluble protein fraction.

The freeze-dried soluble fraction can be analyzed to determine a ratio of the concentration of soluble protein to lipids. Generally, it can be expected that the freeze-dried powdered soluble fraction includes about 87% soluble proteins. If the freeze-dried powdered soluble fraction includes less than about 13% lipids, however, the soluble fraction can be supplemented with lipids from an additional lipid fraction to provide a soluble protein fraction having about 87% soluble proteins and about 13% lipids. The additional lipid fraction can be obtained from the freeze-dried EGS. The therapeutic composition can include the soluble protein fraction having about 87% soluble proteins and about 13% lipids.

For administration of the composition, the soluble protein fraction can be taken out of deep freeze (−80° C.), dissolved in saline in phosphate buffer (pH 7.5), and maintained at temperatures ranging from about 4° C. to about 6° C. to be ready for administration. In an embodiment, the composition includes the soluble protein fraction dissolved in phosphate buffer saline. It is preferable to dissolve the soluble protein fraction and administer the composition when the composition is still cold, e.g., temperatures ranging from about 4° C. to about 6° C. For example, the composition can be maintained in crushed ice or in a refrigerator until it is ready to be administered.

These and other features of the present disclosure will become readily apparent upon further review of the following specification.

BRIEF DESCRIPTION OF THE DRAWINGS

FIG. 1A is a graph showing the effect of fraction B in the growth of human pancreatic cancer Panc-1.

FIG. 1B is a graph showing the effect of fraction B in the growth of BXPC3.

FIG. 1C is a graph showing the effect of fraction B in the growth of mouse pancreatic cancer Panc-02 cells.

DETAILED DESCRIPTION OF THE PREFERRED EMBODIMENTS

Figure 2A:
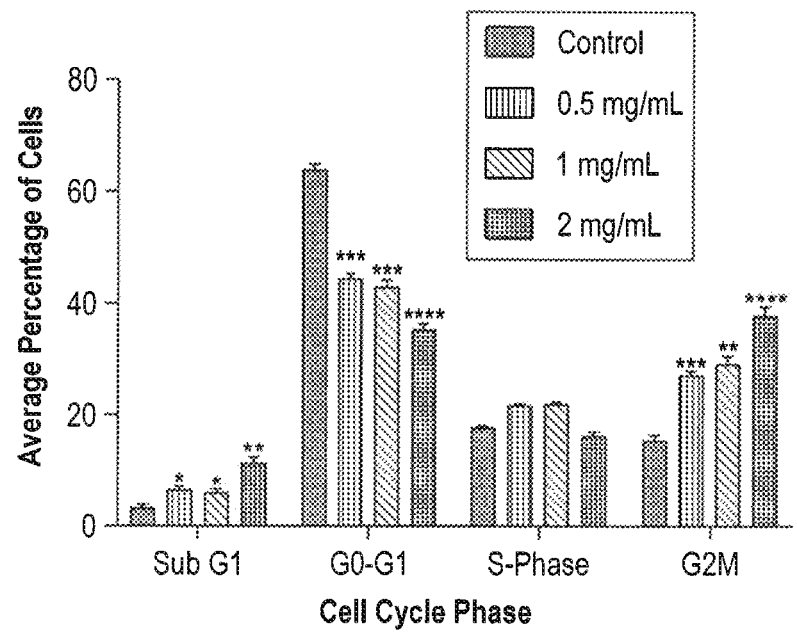
FIG. 2A is a graph showing cell cycle analysis of Panc-1 cells treated with fraction B.

A method of treating cancer can include administering a therapeutically effective amount of a composition comprising a soluble protein fraction obtained from epidermal gel secretions of catfish to a patient in need thereof. The cancer can include at least one of liver cancer and pancreatic cancer. In an embodiment, the cancer includes pancreatic cancer. The soluble protein fraction can include soluble proteins and lipids. The soluble protein fraction can include about 87% soluble proteins and about 13% lipids. The composition can be administered by intraperitoneal (IP) or sub-cutaneous (SC) injection. A method of preparing the soluble protein fraction can include collecting the epidermal gel secretion of catfish and fractionating the epidermal gel secretion to obtain the soluble protein fraction.

A method of preparing a therapeutic composition from the epidermal gelatinous secretion of catfish can include collecting epidermal gel secretions (EGS) from the catfish and fractionating the epidermal gel secretions to obtain a soluble protein fraction comprising about 87% soluble proteins and about 13% lipids. The therapeutic composition can include the soluble protein fraction comprising about 87% soluble proteins and about 13% lipids.

The soluble protein fractions described herein can be obtained from the epidermal gel secretions (EGS) of Arabian Gulf catfish, such as (Arius bilineatus (Valenciennes)). The Arabian Gulf catfish naturally exudes a gelatinous secretion through its skin after the catfish is shocked, e.g., threatened or injured. For example, once a catfish is caught, it will struggle as it is towed to the surface with the fishing hook still in its mouth (as the catfish is a bottom dweller). As the fish reaches the surface, it struggles to defend itself and to escape the reduction in water pressure. This will cause the fish to secrete the EGS along with one or more contaminants, such as venom from its venom glands, faeces from its anal pore, vomit from its mouth and through its gills, and blood through its gills if the fishing hook catches the gill rays. Shocking the fish can also be accomplished by thermal shock, physical abrasions, or neural stimulation. The fish can be washed one or more times to remove contaminants. While the fish is still alive, the fish can be held through its gills to induce production of additional EGS. The EGS without any remaining contaminants on the skin can be collected by a gentle mechanical scraping or suction of the skin. Preferably, the EGS is immediately frozen, e.g., in dry ice, then cooled to −80° C. (deep freeze) or kept frozen in liquid nitrogen, to limit microbial growth and prevent biochemical decomposition.

The soluble protein fractions described herein can include a mixture of highly active biochemical and pharmacological components. These include, for example, a plasma clotting factor that has been found to be specific to blood clotting factor X1, a hemolytic factor, platelet activating factors (PAFs) at unusually high levels (more than 5,000 times the threshold level required for normal platelet activation), and a hemagglutination factor. The soluble fraction can also include vaso-active components, phosphatases, including an acid phosphatase, a general esterase and a tyrosine specific esterase, and proteins with collagenase-like activities that cleave collagen into fragments. The soluble fraction can include a factor that activates phospholipase A2, tyrosine and serine/threonine protein phosphorylase, proteolytic and antimicrobial activities, leukotrienes, interleukin 1 and growth factors that affect macrophages and pancreatic β-cells, along with four protein components that are capable of binding human fibronectin. The lipids in the soluble fraction can include neutral lipids, phospholipids, and glycolipids. For example, the neutral lipids can include eicosanoids, cholesterol, triglycerides, fatty acids and steroids.

It should be understood that a therapeutic composition can be prepared from epidermal gel secretions of other species of catfish or any other aquatic or terrestrial creature (e.g., moray eels, slugs, and worms) that produces epidermal gel secretions having biologically active components similar to those present in the soluble protein fractions described herein.

As used herein, the term "about," when used to modify a numerical value, means within ten percent of that numerical value.

According to an embodiment, the method of preparing a therapeutic composition from the epidermal gelatinous secretion of catfish can include collecting epidermal gel secretions (EGS) from the skin of Arabian Gulf catfish (Arius bilineatus (Valenciennes)) and fractionating the EGS to provide a soluble protein fraction (SPF).

In an embodiment, the soluble protein fraction (SPF) can be extracted from the EGS by thawing the frozen EGS to a temperature ranging from about 4° C. to about 6° C. and mixing the thawed EGS with a suitable, non-toxic extraction buffer (e.g., saline in phosphate buffer at pH 7.5) to provide an extract. This step and all subsequent purification procedures can be carried out at about 4° C. to about 6° C. in the dark, unless otherwise indicated. The extraction buffer should not denature or affect the proteins in the EGS in any way. Preferably, the extraction buffer includes phosphate buffered saline having 0.05M ($NaH_2PO_4/Na_2HPO_4$) and 0.14M NaCl, pH 7.5. The thawed EGS can be mixed with an equal volume of the extraction buffer and homogenized, e.g., with an Ultra Truex (IKA) homogenizer. The homogenized extract can then be centrifuged to provide a soluble protein fraction (SPF) and an insoluble protein fraction. Centrifugation can separate insoluble filamentous proteins and cellular debris from a soluble fraction. Centrifugation can also remove contaminants such as microorganisms. The therapeutic composition is preferably free from insoluble components, as such components are not appropriate for intraperitoneal or sub-cutaneous injection and will not be absorbed and distributed if injected into an animal or human in this manner. Insoluble components can also clog the injection needle during injection. In an embodiment, the homogenate is centrifuged at 15,000 rpm for about ten to about fifteen minutes to provide the soluble fraction and the insoluble fraction. The soluble fraction can be freeze-dried and maintained at about −80° C. under nitrogen.

In an embodiment, the soluble protein fraction is freeze-dried and maintained at about −80° C. under nitrogen. The freeze-dried soluble fraction can be analyzed to determine a ratio of the concentration of soluble protein to lipids. In an embodiment, the powdered soluble fraction includes about 87% soluble proteins and about 13% lipids. If the powdered soluble fraction includes less than about 13% lipids, the powdered soluble fraction can be supplemented with lipids from an additional lipid fraction to achieve a soluble protein fraction having about 87% soluble proteins and about 13% lipids. The additional lipid fraction can be obtained from the freeze-dried EGS, as described herein. The therapeutic composition can include the soluble protein fraction having about 87% soluble proteins and about 13% lipids. The soluble fraction (SPF) (also referred to herein as "Fraction B") can be freeze-dried and stored at about −80° C. under nitrogen.

According to an embodiment, an additional soluble protein fraction can be separated from the insoluble fraction obtained from centrifugation. According to an embodiment, an insoluble fraction obtained from centrifugation in one fractionating cycle can be further fractionated in a subsequent fractionating cycle to provide yet another soluble protein fraction. According to an embodiment, the method can include about two to about four fractionating cycles of insoluble protein fractions, thereby providing a plurality of additional soluble protein fractions. The plurality of additional soluble protein fractions can be pooled and added to the original SPF obtained from the original fractionation of the EGS. The soluble protein fraction (SPF) or "Fraction B" can include the pooled soluble protein fractions. The SPF can be used for IP injection in an animal or human for treating cancer. The SPF (Fraction B) can include lipids as well as soluble proteins (about 87% soluble proteins and about 13% lipids).

The concentration of lipids in the soluble protein fraction can be determined, e.g., by extracting the lipids from a freeze-dried soluble protein fraction and weighing the extracted lipids. If the soluble protein fraction includes about 87% soluble proteins, but less than about 13% lipids, additional lipids can be extracted directly from an EGS and added to the freeze-dried soluble protein fraction to increase the lipid percentage to about 13%. The additional lipids can be extracted from the freeze-dried original EGS. As described in detail, below, lipid extraction can be carried out in the dark and the extracted lipids can be stored under nitrogen until added to the soluble protein fraction. The lipids can be added with an organic solvent, e.g., isopropyl alcohol, to the freeze-dried soluble protein fraction to increase the lipid concentration to about 13% of the total soluble protein-lipid fraction. The organic solvent can be evaporated under vacuum at room temperature.

In an embodiment, if it is determined that the soluble protein fraction includes about 87% soluble proteins but less than about 13% lipids (which is generally the case), additional lipids can be provided by extracting lipids from the EGS with an organic solvent mixture. The additional lipids can be obtained from the freeze-dried EGS by extracting the lipids with an organic solvent mixture including chloroform:methanol:isopropanol (2:1:0.250, v/v) for about 72 hours on a stirring plate. The extracted lipids can then be obtained by filtration, e.g., using a vacuum pump and a Buchner funnel. The lipid extracts can be concentrated to dryness on a rotary evaporator at about 25° C. in the dark and weighed to ensure that the required weight of lipids to be added to the soluble protein fraction is achieved. The required amount of lipids can be dissolved in a suitable organic solvent, e.g., isopropyl alcohol, and added to the soluble freeze-dried protein fraction to increase the lipid fraction in the soluble protein fraction to about 13% of the combined weight of the proteins and lipids. The organic solvent can be evaporated under vacuum at room temperature in the dark to provide a freeze dried soluble protein fraction having about 87% soluble proteins and about 13% lipids of the total combined soluble proteins and lipids. The freeze dried soluble protein fraction (soluble proteins combined with the lipids) can be stored under nitrogen at about −80° C. until needed for injection. The freeze dried soluble fraction can be maintained at about −80° C. (deep freeze) for long-term storage to prevent any unwanted chemical reaction. The enzymes in the fraction will not react against the components in the fraction if kept at about −80° C. during storing for lengthy periods of time under nitrogen. Also the lipids in the soluble protein fraction will be protected from decomposition if kept the same way in deep freeze until required for use. Nitrogen will not allow aerial oxygen to react with the lipids. The SPF is preferably stored in portions appropriate for a single injection at −80° C. It can then be thawed, kept in ice, and administered as needed.

A therapeutically effective amount of the composition including the SPF (Fraction B) can be administered to a patient to treat cancer. For example, administering the composition to a patient can inhibit the growth of cancer cells. A therapeutically effective amount can include about 3 mg to about 3.5 mg of the SPF (e.g., SPF including about 85% soluble protein and about 13% total lipids) per 100 gm of body weight of the patient (animal or human) to be treated. The cancer can include at least one of liver cancer and pancreatic cancer. The therapeutic composition can be administered to a patient in need thereof, preferably by intraperitoneal (IP) or sub-cutaneous (SC) injection after dissolution of the SPF in saline, phosphate buffered saline, or other delivery system, such as nanotechnology delivery systems. The therapeutic composition can be combined with a pharmaceutically acceptable carrier. The therapeutic composition can be administered using other delivery methods, e.g., oral administration, provided that the composition is protected from the digestive effects of the elementary canal for oral administration, such as by encapsulation or nanoparticle technology. Prior to injection of the soluble protein fraction, the freeze-dried soluble fraction can be dissolved in saline, phosphate buffered saline.

As described herein, the composition including the SPF (Fraction B) was injected inter peritoneally (IP) at a concentration of 0.3-0.3.5 mg protein/100 g body weight in mice bearing Panc-1 and Panc-02 tumors. The animals were then assessed for the size of the tumour. It was found that the tumour size decreased in response to treatment with Fraction B. After 10 days, the animals were sacrificed and histological and biochemical studies were conducted on the pancreas. These studies confirmed the apoptotic, anti-proliferative, and anti-inflammatory actions of SPF (Fraction B). Table 1 shows blood chemistry parameters in control mice bearing Panc-1 cells tumor and Fraction B treated mice bearing Panc-1 cells tumor. Table 2 shows the complete blood count (CBC) for the control mice bearing Panc-1 cells tumor and Fraction B treated mice bearing Panc-1 cells tumor.

TABLE 1

| Name of tests | Control | Fraction B (6 mg/kg) |
| --- | --- | --- |
| Albumin | 3.02 ± 0.13 | 2.91 ± 0.29 |
| Alk. Phoph | 38.83 ± 13.99 | 47.83 ± 4.21 |
| ALT | 34.00 ± 9.61 | 36.00 ± 6.87 |

TABLE 1-continued

| Name of tests | Control | Fraction B (6 mg/kg) |
|---|---|---|
| AST | 91.83 ± 23.52 | 79.50 ± 15.74 |
| BUN | 29.63 ± 2.76 | 28.47 ± 3.62 |
| Creatine | 0.22 | <0.20 |
| Globulin | 1.94 ± 0.34 | 2.18 ± 0.64 |
| Total protein | 4.96 ± 0.29 | 5.10 ± 0.53 |

TABLE 2

| Name of Tests | Control | Fraction B |
|---|---|---|
| WBCC | 11.67 ± 3.28 | 12.37 ± 1.85 |
| RBCC | 8.99 ± 0.78 | 8.45 ± 0.51 |
| Hemoglobin | 13.30 ± 0.94 | 12.53 ± 0.79 |
| Hematocrit | 43.67 ± 2.93 | 40.90 ± 2.40 |
| MCV | 48.70 ± 1.31 | 48.45 ± 0.93 |
| MCH | 14.83 ± 0.45 | 14.85 ± 0.24 |
| MCHC | 25.89 ± 11.19 | 30.63 ± 0.25 |
| RDW | 16.07 ± 0.61 | 16.45 ± 0.51 |
| Platelet | 1471.17 ± 143.74 | 1424.00 ± 193.45 |
| MPV | 5.37 ± 0.10 | 5.25 ± 0.14 |
| Segs | 40.58 ± 11.94 | 37.80 ± 5.26 |
| Lympha | 50.43 ± 12.48 | 53.03 ± 5.32 |
| Monos | 4.07 ± 0.98 | 4.93 ± 1.08 |
| Eos | 2.57 ± 1.24 | 2.60 ± 0.70 |
| Basos | 0.43 ± 0.14 | 0.38 ± 0.08 |
| LUC | 1.88 ± 1.15 | 1.23 ± 0.38 |

The following examples illustrate the present teachings.

Example 1

Preparation of SPF and Calculation of Soluble Protein in Solution

EGS was collected from the catfish skin and kept at −80° C. until use. Frozen EGS was thawed to 4° C., mixed with an equal volume of extraction buffer [phosphate buffered saline (PBS), 0.05 M containing ($NaH_2PO_4Na_2HPO_4$) and 0.14 M NaCl, pH 7.5], and homogenized with an Ultra Truex (IKA) homogenizer. This step and all subsequent purification procedures were carried out at 4° C. unless otherwise indicated. The homogenate was centrifuged at 15,000 rpm for 15 minutes. The supernatant was collected, and the pellet (insoluble protein etc.) was re-extracted with extraction buffer (2-4 times for different exemplary compositions). Each time, the soluble fraction was separated by centrifugation as described above, and the two extracted fractions were pooled. The combined extracted fractions provided the soluble protein fraction (SPF) (Fraction B).

To find the concentration of catfish soluble proteins in the SPF (Fraction B), the SPF was diluted with PBS (1:50). 0.1 ml of the diluted sample was mixed well with 5 ml of Coomassie Brilliant Blue solution and kept in tubes at room temperature for about 10 minutes. Absorbance was read at 595 nm for the sample, and its protein concentration was determined by comparing its absorbance against absorbance for a standard curve for different bovine serum albumin concentrations. Fraction B was found to include about 85% soluble proteins and about 13% lipids.

The SPF (Fraction B) was then dissolved in the extraction buffer and diluted with saline for injection.

Example 2

Effect of Fraction B on Human and Mouse Pancreatic and Liver Cancer Cells

To understand whether fraction B has the ability to inhibit proliferation of human cancer cells, especially pancreatic cancer and liver cancer, the effect of Fraction B in the proliferation of mouse Panc-02 cells and human pancreatic cancer Panc-1 and BxPC3 cells as well as human liver cancer Hep3B cells was studied. Intriguingly, all four cell lines responded to Fraction B treatment dose-dependently with very similar potency with IC50 for all four cell lines being at 200-400 μg/kg. The results suggested that the anti-proliferative effect of Fraction B in human pancreatic and liver cancer cells is mediated through similar mechanisms (FIGS. 1A-1C).

Example 3

Figure 2B:
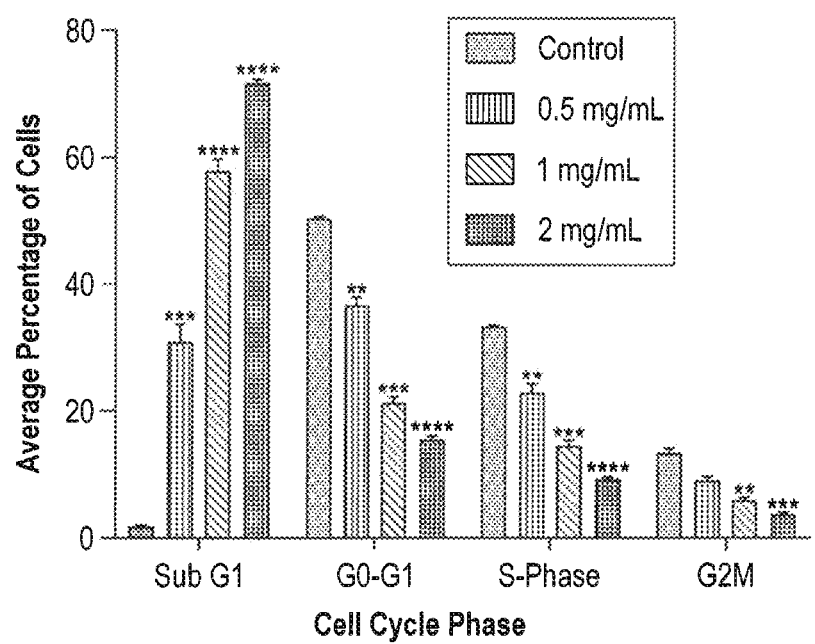
FIG. 2B is a graph showing cell cycle analysis of Panc-02 cells treated with fraction B.

Determining Whether Fraction B Inhibits Growth of Panc-01 Cells and Panc-02 Cells Through Apoptosis To determine whether the inhibitory effect of Fraction B upon cancer cell growth is mediated through reducing cell proliferation or induction of apoptotic cell death, cell cycle and apoptotic cell death in Fraction B treated Panc-1 and Panc-02 cells were measured by propidium iodine staining. As shown in FIGS. 2A and 2B, Fraction B (500 μg/ml) significantly increased subG1/G0 phase cells by 2-fold and 25 fold in Panc-1 cells and Panc-02 cells respectively, vs. vehicle treatment, suggesting that the cells were undergoing apoptosis.

Example 4

Figure 3A:
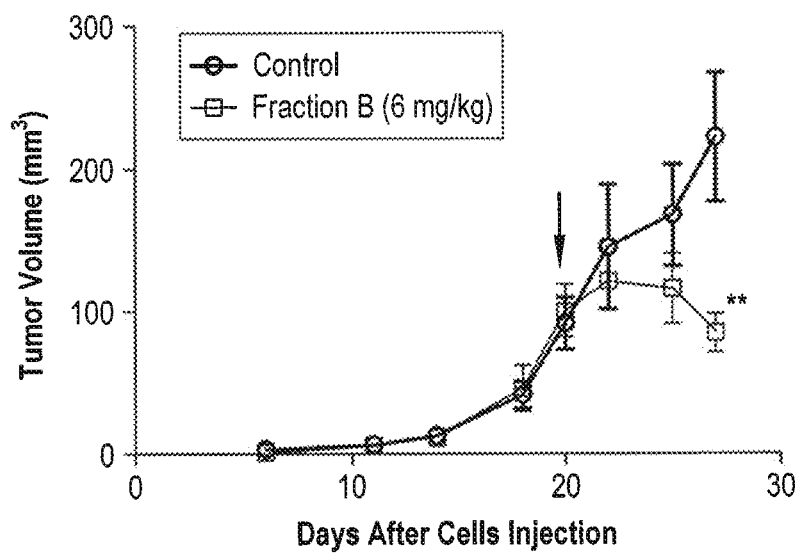
FIG. 3A is a graph showing the growth curve of Panc-02 tumor development after being treated with Fraction B.
Figure 3B:
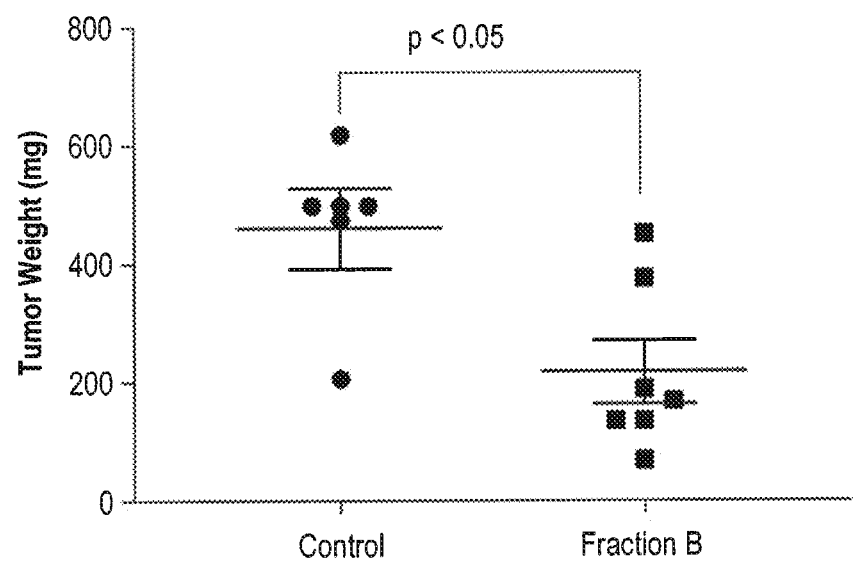
FIG. 3B is a graph showing terminal tumor weight of Panc-02 after being treated with Fraction B. P<0.01 treated versus control.
Figure 4A:
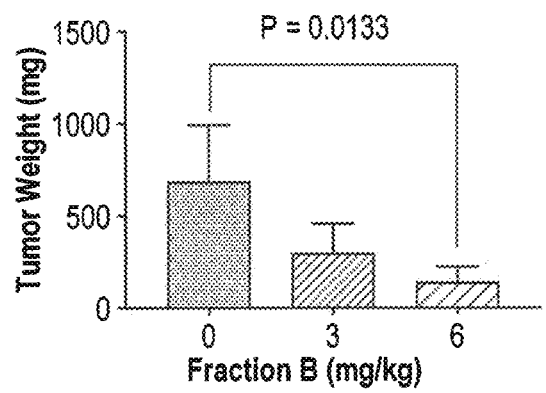
FIG. 4A is a graph showing the terminal weight of human pancreatic cancer Panc-1 tumor after administration of Fraction B.
Figure 4B:
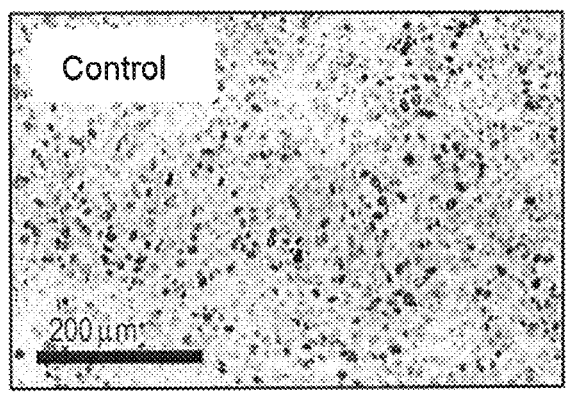
FIG. 4B shows proliferative cancer cells stained with nuclear staining marker Ki67 in control tumor.
Figure 4C:
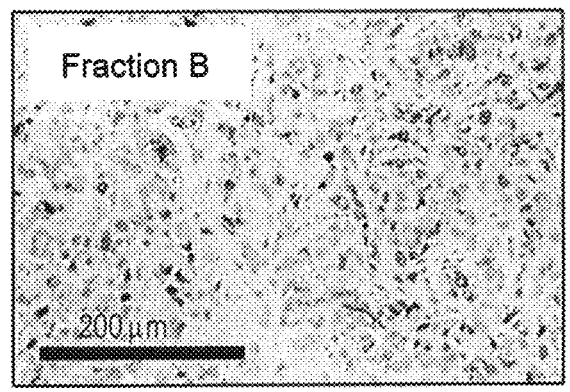
FIG. 4C shows proliferative cancer cells stained with nuclear staining marker Ki67 in Fraction B treated tumor.

Effect of Fraction B on Growth of Panc-02 Mouse Syngeneic Tumor and Human Panel Mouse Orthotopic Model To further evaluate the efficacy of Fraction B in pancreatic cancer, an antitumor efficacy study was conducted in a mouse pancreatic cancer Panc-02 syngeneic model and human Panc-1 orthotopic model. The antitumor effect of Fraction B in mouse pancreatic cancer Panc-02 syngeneic model was first tested as this model was established in mice with an intact immune system and because this is considered a relatively aggressive pancreatic cancer model. Panc-02 cells ($5×10^4$) were injected to the right flank of C57/B6 mice (n=7-9 per group). When tumors were approximately 50-100 $mm^3$, Fraction B was administered via i.p injection daily for two weeks. Tumor was measured by caliper and tumor volume was calculated with $a*b^2/2$, in which b is shorter than a. Mice tolerated the treatment very well without any sign of toxicity in this model. As shown in FIGS. 3A-3B, Fraction B significantly suppressed the growth of Panc-02 tumor (p<0.01). In fact, the treatment actually led to tumor regression after only two weeks of treatment (FIG. 3A). The average terminal tumor weight of mice treated with Fraction B (6 mg/kg) was 218.1±53.1 mg, which was 53% smaller than that of control group (460.2±68.0 mg) (p<0.05) (FIG. 3B). Given Panc-02 tumor is a well-known and very aggressive pancreatic tumor model, these data strongly suggest Fraction B has a great potential to be developed as an anti-cancer agent for the treatment of pancreatic cancer. The antitumor activity of Fraction B in human pancreatic cancer Panc-1 mouse orthotopic model was then evaluated to determine whether the tumor growing in the physiologically relevant environment would respond to the treatment of Fraction B in a manner similar the manner in which the mouse pancreatic panc-02 tumor responded. The tumor size was determined by MRI 10 days after tumor cells were injected in the mice pancreas and the mice were then randomized to either control or treatment group. As shown in FIG. 4A, The average tumor weight of mice treated with Fraction B (6 mg/kg) was 139.5±34.0 mg, which was significantly 80% less than that of control group (686.1±306.7 mg) ($p<0.05$). Similarly, MRI imaging also demonstrated that mice bearing Panc-1 tumor treated with Fraction B showed smaller tumors compared to that of control mice (FIGS. 4B-4C). Together, this data strongly suggests that Fraction B would have great potential to be developed as an anticancer agent for the treatment of pancreatic cancer.

Example 5

Effect of Fraction B on Inhibition of Cancer Cell Proliferation

Figure 4D:
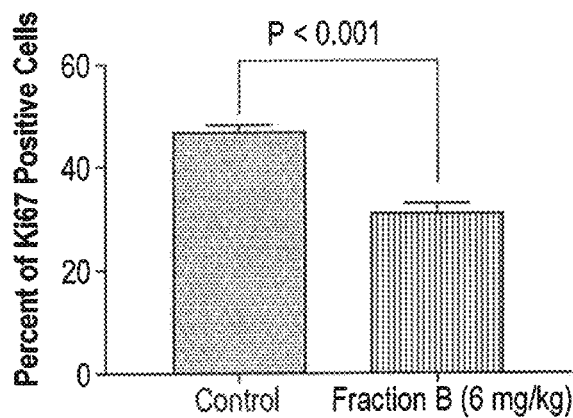
FIG. 4D is a graph showing percentage of Ki67 positive cells in the control and Fraction B-treated tumor.
Figure 5:
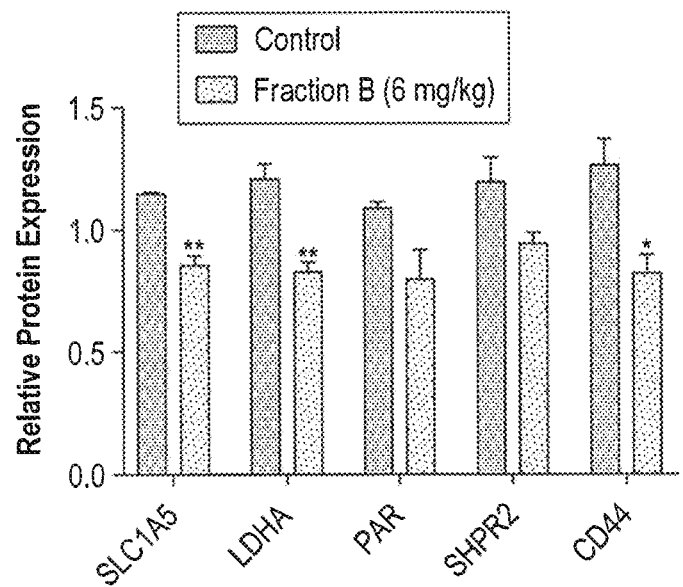
FIG. 5 is a graph showing the expression of proteins associated with glutamine metabolism, such as SLC1A5, glycolysis (LDHA) and stem cell markers of pancreatic cancer (CD44) in Panc-1 human tumor tissues assessed by the Reverse Phase Proteomic Array.

The proliferation status of Panc-1 tumor treated with Fraction B was then examined by staining the tissue with Ki67, the nuclear marker for cell proliferation. As shown in FIG. 4D, the percentage of Ki67 positive cells in Fraction B-treated Panc-1 tumor (31.0±2.1%) was significantly lower than that of control treated tumor (46.8±1.4%), suggesting Fraction B indeed was capable of inhibiting proliferation of Panc-1 tumor cells.

Example 6

Figure 6A:
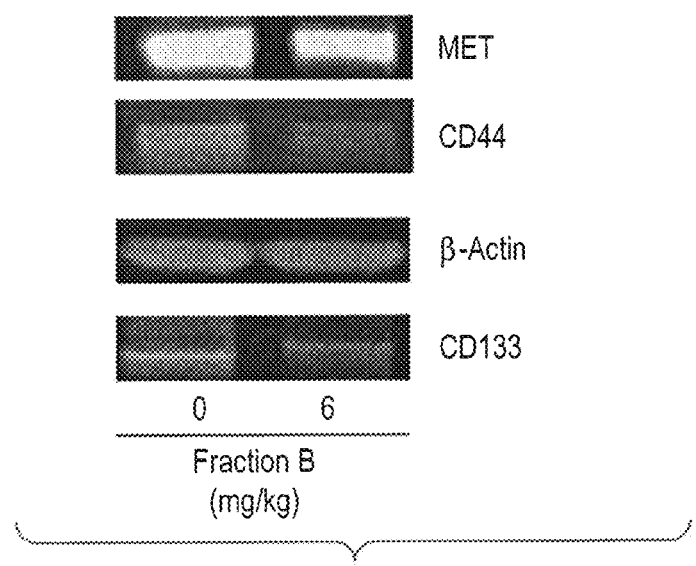
FIG. 6A is a Western blot image showing protein expression in Fraction B treated Panc-1 tumor tissues.
Figure 6B:
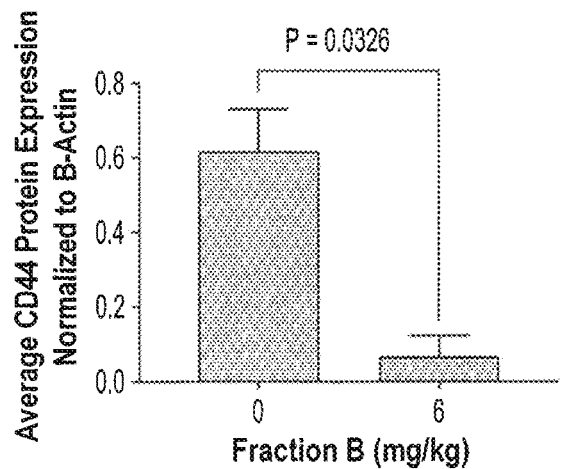
FIG. 6B is a graph showing the average CD44 protein expression normalized to B-Actin.
Figure 6C:
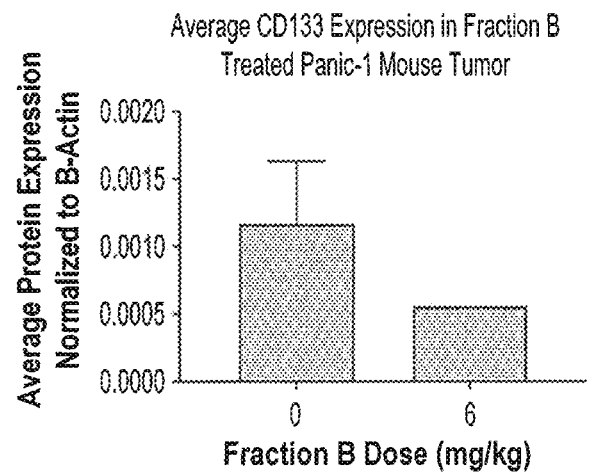
FIG. 6C is a graph showing the average CD133 expression in Fraction B-treated Panc-1 mouse tumor.
Figure 6D:
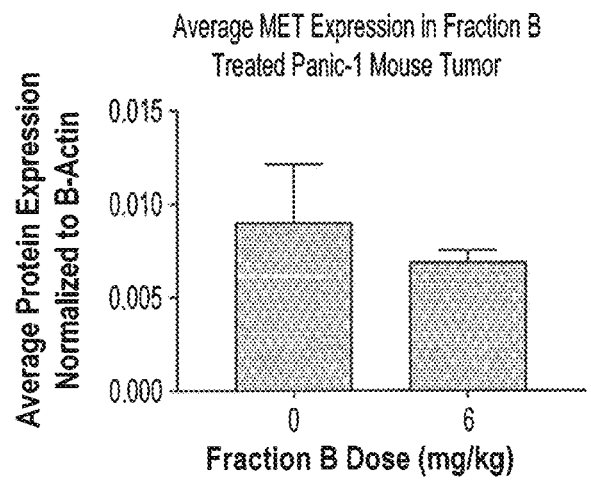
FIG. 6D is a graph showing the average MET expression in Fraction B-treated Panc-1 mouse tumor.
Figure 8:
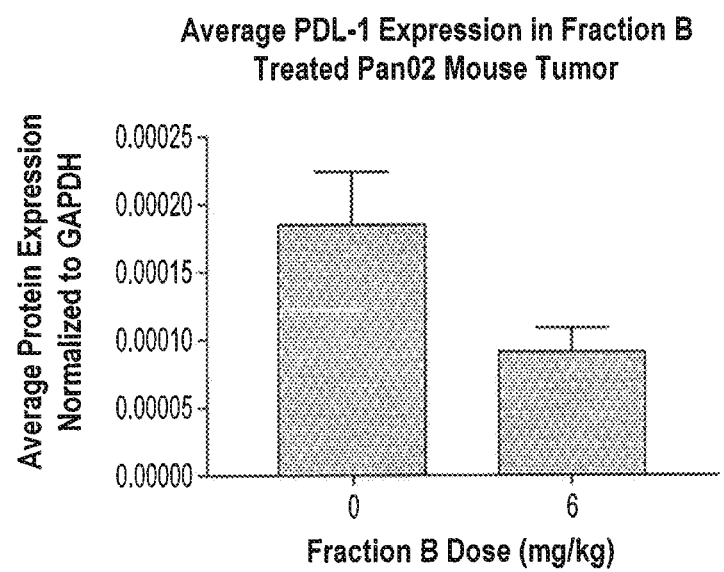
FIG. 8 is a graph showing the average PDL-1 expression in Fraction B treated Panc-02 mouse tumor.

Effect of Fraction B on Proteins Mediating Cancer Cell Stemness and Cancer Cell Metabolism in Panc-1 Tumor Tissues To understand the mechanism in which Fraction B elicited anticancer activity in pancreatic cancer, we analyzed apoptotic, cell cycle and cell signaling proteins in Panc-1 tumor tissue treated with Fraction B and that of controls using Reverse Phase Proteomic Array (RPPA). As shown in FIGS. 5 and 6B-6D, among numerous proteins affected by Fraction B, Fraction B treatment (6 mg/kg) significantly down-regulated CD44 by 54%, a known stem cells marker, LDHA, by 44%, a key glycolytic enzyme, SCL1A5, by 33%, a glutamine transporter, and two phosphorylated S6 proteins which was a downstream target of mTOR pathways, suggesting Fraction B elicited antitumor activity is due to suppression of both cancer stemness and reducing energy related pathways. The remarkable inhibitory effect of Fraction B on pancreatic cancer stem cell markers, such as CD44, CD133 and Met was further confirmed by western blotting in Fraction B treated Panc-1 tumor tissues (FIG. 6A) which again supported that Fraction B inhibited the tumor growth potentially through reducing the stemness of pancreatic cancer cells. FIG. 8 shows the average PDL-1 expression in Fraction B treated Panc-02 mouse tumor.

Example 7

Effect of Fraction B on Glycolysis and Glutamine Metabolism in Panc-1 Tumor

Figure 7A:
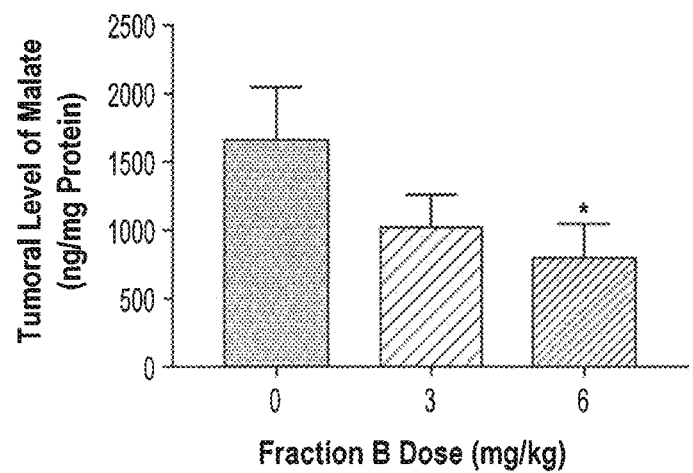
FIG. 7A is a graph showing the tumoral level of malate in Panc-1 tumor tissues treated with Fraction B.
Figure 7B:
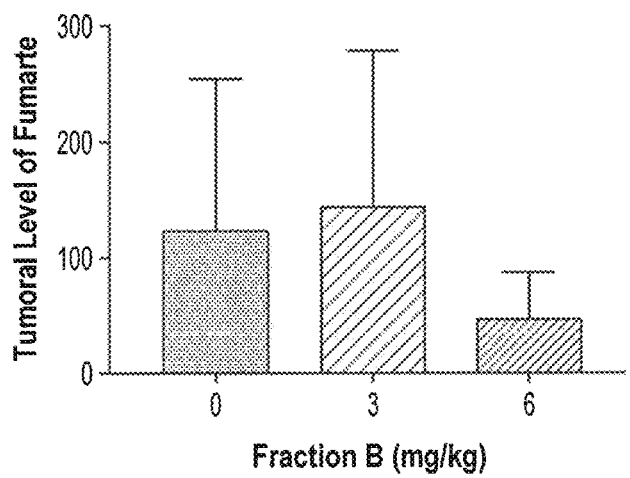
FIG. 7B is a graph showing the tumoral level of fumarate in Panc-1 tumor tissues treated with Fraction B.
Figure 7C:
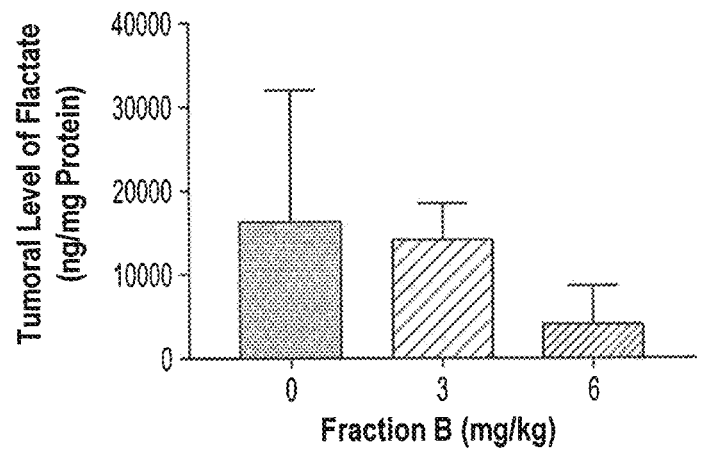
FIG. 7C is a graph showing the tumoral level of lactate in Panc-1 tumor tissues treated with Fraction B.
Figure 7D:
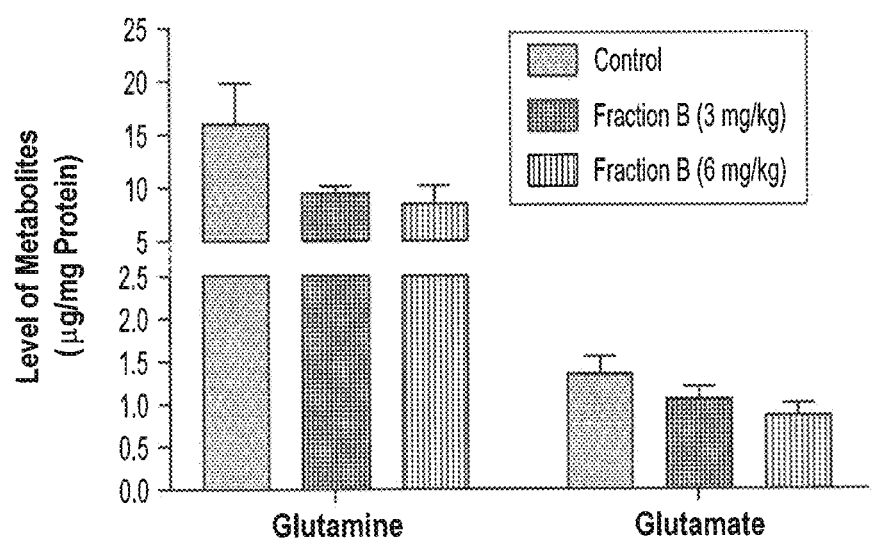
FIG. 7D is a graph showing the level of glutamine and glutamate in Panc-1 tumor tissues treated with Fraction B.
Figure 7E:
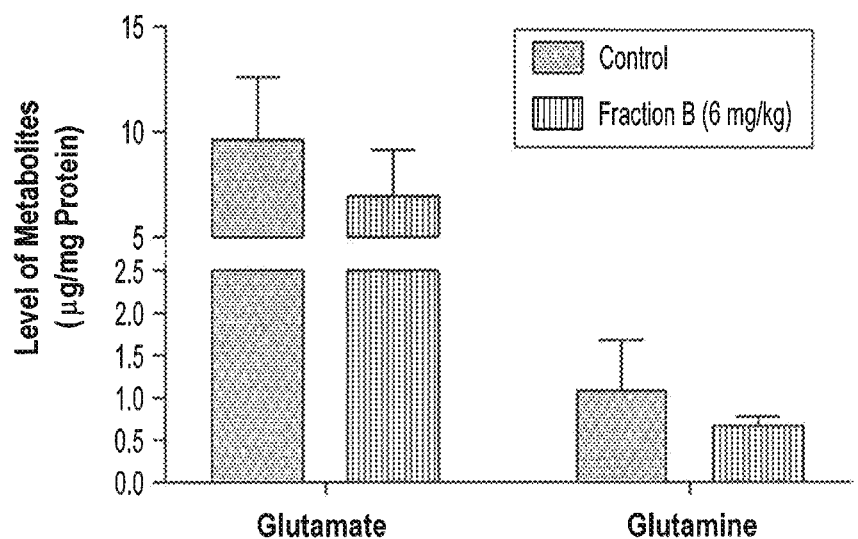
FIG. 7E is a graph showing the level of glutamine and glutamate in Panc-02 tumor tissues treated with Fraction B.

Both glucose and glutamine metabolisms are essential for the proliferation of cancer cells (Halbrook C J, Cancer Cells, 2017), especially pancreatic cancer cells. As discussed previously, Fraction B down-regulated protein abundance of the LDHA, enzymes responsible for conversion of pyruvate to lactate, and SCL1A5, a glutamine transporter protein. The level of glycolysis metabolites and glutamine metabolites was examined using the sensitive and specific analytical method developed in our lab using LC/MS/MS instrument (Wang Y G, Nature, 2017). LC/MS/MS analysis confirmed that Fraction B significantly reduced glucose metabolites involved in glycolysis and TCA cycle, including lactate, malate and furmarate in Panc-1 tumor tissues compared to that of control tumor tissues (FIGS. 7A-7C). The tumoral levels of glutamine and glutamate in Fraction B (6 mg/kg) treated mice were 47% and 36%, respectively lower than those from control groups (FIG. 7D), suggesting Fraction B does dependently reduce both glycolysis and glutamine metabolism in human Panc-1 tumor. In contrast, the levels of glutamine and glutamate were reduced by 40% in Fraction B treated Panc-02 tumor (FIG. 7E), suggesting the impact of metabolic changes elicited by Fraction B in Panc-1 and Panc-02 tumor is different, which deserves further investigation.

Example 8

Effect of Fraction B on Safety Profile in Mouse Bearing Panc-1 Tumor

While Fraction B showed promising antitumor efficacy in both mouse Panc-02 and human Panc-tumor models, it was determined that the safety of the composition should be tested. It was previously noted that there were not any body weight changes in the mice treated with Fraction B compared to that of control mice. In order to determine the safety profile of Fraction B, the blood of mice from the Panc-1 tumor study was collected and subjected to CBC and blood chemistry analysis by the pathological core facility at the Department of Veterinary Medicine at MDACC. The result of CBC and blood chemistry analysis showed that Fraction B did not cause any substantial changes on blood count, liver and kidney function (Table 1), suggesting Fraction B is relatively safe to be administered.

It is to be understood that the method for treating cancer is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method for treating liver or pancreatic cancer, comprising:
    providing a therapeutic composition, the therapeutic composition including a soluble protein fraction prepared by fractionating epidermal gel secretions of catfish, the soluble protein fraction including about 87% soluble proteins and about 13% lipids; and
    administering a therapeutically effective amount of the therapeutic composition to a patient suffering from liver or pancreatic cancer,
    wherein the therapeutically effective amount of the composition includes about 3 mg to about 3.5 mg of the soluble protein fraction per 100 gm of body weight of the patient.

2. The method according to claim 1, wherein the fractionating comprises:

mixing the epidermal gel secretions with an extraction buffer to provide an extract;
homogenizing the extract with a homogenizer to provide a homogenate; and
centrifuging the homogenate to provide the soluble protein fraction and an insoluble protein fraction.

3. The method according to claim 1, wherein the extraction buffer comprises phosphate buffered saline.

4. The method according to claim 1, wherein the catfish is Arabian Gulf catfish.

5. The method according to claim 1, wherein the therapeutic composition is administered by subcutaneous injection.

6. The method according to claim 1, wherein the therapeutic composition is administered by intraperitoneal injection.

\* \* \* \* \*